United States Patent
Lewis

(10) Patent No.: US 7,651,635 B1
(45) Date of Patent: Jan. 26, 2010

(54) POLYMER INHIBITION OF VINYL AROMATIC MONOMERS USING A QUINONE METHIDE/ALKYL HYDROXYLAMINE COMBINATION

(75) Inventor: Vincent E. Lewis, Missouri City, TX (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 12/366,154

(22) Filed: Feb. 5, 2009

(51) Int. Cl.
*C09K 15/08* (2006.01)
*C07C 7/20* (2006.01)
*C08F 2/00* (2006.01)

(52) U.S. Cl. ............ 252/403; 252/404; 252/182.13; 252/182.29; 526/77; 585/4

(58) Field of Classification Search ........... 526/77; 252/403, 404, 182.13, 182.29; 585/4
See application file for complete search history.

(56) References Cited

U.S. PATENT DOCUMENTS

| | | | | |
|---|---|---|---|---|
| 3,390,198 | A | * 6/1968 | Leston | 585/3 |
| 4,003,800 | A | 1/1977 | Bacha et al. | |
| 4,409,408 | A | * 10/1983 | Miller | 585/4 |
| 5,446,220 | A | 8/1995 | Arhancet | |
| 5,583,247 | A | 12/1996 | Nesvadba et al. | |
| 6,024,894 | A | 2/2000 | Arhancet | |
| 7,045,647 | B2 | 5/2006 | Benage | |

* cited by examiner

*Primary Examiner*—Fred M Teskin
(74) *Attorney, Agent, or Firm*—Benjamin E. Carlsen; Michael B. Martin

(57) ABSTRACT

The invention provides a composition of matter and a method of its use in preventing unwanted polymerization reactions. The composition comprises an inhibitor and a retarder. The inhibitor is highly effective. The retarder is reliable under extreme and emergency situations. The inhibitor can be an alkylhydroxylamine. The retarder can be a 7-cyano-quinone methide. The combination of the inhibitor and retarder has been found to be far more effective than expected.

16 Claims, No Drawings

POLYMER INHIBITION OF VINYL AROMATIC MONOMERS USING A QUINONE METHIDE/ALKYL HYDROXYLAMINE COMBINATION

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to compositions of matter and methods of using them to inhibit the polymerization of vinyl aromatic monomers. Many of these monomers undesirably polymerize at various stages of their manufacture, processing, handling, storage, and use. These undesirable polymerization reactions result in a loss in production efficiency because they consume valuable reagents and because they require additional purification steps to remove the undesired polymers. Undesired polymerization reactions are particularly problematic by vinyl aromatic monomers and form unwanted polymer during the purification process.

Two categories of compounds have been developed to prevent unwanted polymerization reactions, inhibitors and retarders. Inhibitors prevent polymerization reactions from occurring. Inhibitors however are consumed rapidly. In cases of emergency when for a mechanical or other reason more inhibitor cannot be added, previously added inhibitor will be rapidly consumed and the unwanted polymerization reactions will then rapidly recur. Retarders slow down the rate of polymerization reactions but are not as effective or as inhibitors. Retarders however are usually not consumed as quickly so they are more reliable in cases of emergency.

At first only retarders such as sulfur, and dinitrophenols (DNP) (including 2,6-dinitrophenol, 2,4-dinitrocresol, and 2-sec-butyl-4,6-dinitrophenol (DNBP)) were used to prevent unwanted polymerization reactions. Later two classes of inhibitors were used dialkylhydroxylamines (including hydroxypropylhydroxyamine (HPHA)) and nitroxides (so-called stable free radicals). Because of safety concerns in the event of a plant malfunction, inhibitors alone cannot be used and they therefore are often combined with retarders.

DNP retarders however are highly toxic and there is a significant need for a replacement for them. One class of compounds that was hoped can be a retarder in the place of DNP are quinone methides. Quinone methides slow the rate of polymer formation under static conditions and do not need to be frequently re-fed. However quinone methides must be used in fairly high dosages, so they are not very economical to use by themselves. Examples of quinone methide compounds are in U.S. Pat. No. 4,003,800. These compound however are not stable enough for sustained use in industrial settings. Other applications of quinone methides are found in U.S. Pat. Nos. 5,583,247, and 7,045,647.

Previous examples of inhibitor-retarder combinations that do not use DNP are U.S. Pat. Nos. 5,446,220 and 6,024,894. These combinations were found to be more effective than DNP alone. They were however found to be less effective than the previous DNP-nitroxide or DNP-dialkylhydroxylamines combinations. Thus there still remains a need for a non-toxic inhibitor-retarder combination for use in preventing the premature polymerization of styrene and other vinyl aromatic monomers.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists. Any and all patents, patent applications, and other references cited by this application are hereby incorporated by reference in their entirety.

BRIEF SUMMARY OF THE INVENTION

At least one embodiment of the invention is directed towards a method for inhibiting the premature polymerization of vinyl aromatic monomers by adding to the monomers an effective amount of a composition comprising at least one inhibitor and at least one retarder. The retarder is a substituted quinone methide.

At least one embodiment of the invention is directed towards a method in which the retarder is selected from the list consisting of: 2,6-di-t-butyl-7-cyano quinone methide, 2,6-di-t-butyl-7-carboxy quinone methide, 2,6-di-t-butyl-7-methoxycarbonyl quinone methide, and any combination thereof. The inhibitor can be an alkylhydroxylamine. The retarder can be non-toxic. The inhibitor can have a dosage of between 1 to 200 ppm, based on the weight of the monomer. The retarder can have a dosage of between 1 to 1200 ppm, based on the weight of the monomer.

At least one embodiment of the invention is directed towards a method in which the inhibitor and retarder are added separately to the monomer. The amount of inhibitor in the presence of the monomers can be maintained at a relatively constant amount by adding the inhibitor in increments over time. The inhibitor can be added intermittently or continuously and can be continuously dispersed throughout the monomer. The inhibitor can be selected from the list consisting of an alkylhydroxylamine such as hydroxypropylhydroxylamine, diethylhydroxylamine, and any combination thereof.

DETAILED DESCRIPTION OF THE INVENTION

In at least one embodiment the premature polymerization of styrene in prevented by the addition of an inhibitor-retarder combination.

For purposes of this application the definition of "induction time" is the period of time in which in an ideal closed system a composition of matter completely prevents the formation of a particular polymer during a given reaction.

For purposes of this application the definition of "inhibitor" is a composition of matter that inhibits the formation of the particular polymer during an induction time but after the induction time has lapsed, the particular polymer's formation occurs at substantially the same rate that it would formed at in the absence of the composition of matter.

For purposes of this application the definition of "retarder" is a composition of matter, which does not have an induction time, but instead once added to the given reaction the composition of matter reduces the rate at which the formation of the particular polymer occurs relative to the rate at which it would have formed in the absence of the composition of matter.

In at least one embodiment the inventive inhibitor is an alkylhydroxylamine selected from the list consisting of hydroxypropylhydroxylamine and diethylhydroxylamine and the inventive retarder is a 7-substituted-quinone methide. The 7-substituted-quinone methides is selected from the list consisting of a 2,6-di-t-butyl-7-cyano quinone methide, a 2,6-di-t-butyl-7-carboxy quinone methide, and a 2,6-di-t-butyl-7-methoxycarbonyl quinone methide.

For purposes of this application, the definition of "2,6-di-t-butyl-7-cyano quinone methide" is a molecule according to the formula:

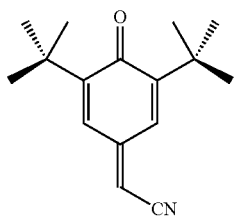

For purposes of this application, the definition of "2,6-di-t-butyl-7-carboxy quinone methide" is a molecule according to the formula:

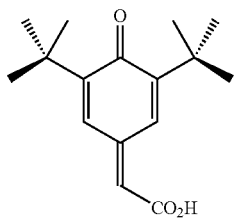

For purposes of this application, the definition of "2,6-di-t-butyl-7-methoxycarbonyl quinone methide" is a molecule according to the formula:

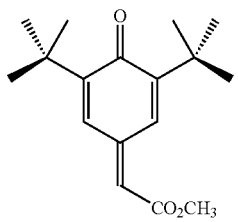

For temperatures of up to 120° C., the effective amount of the combination of alkylhydroxylamine compound is typically about 1 to 200 ppm, based on the weight of the monomer. The effective amount of the combination of 7-cyano-quinone methide is typically about 1 to 400 ppm, based on the weight of the monomer. Amounts outside this range may be appropriate depending upon the conditions of use. For higher temperatures, the effective dosages will be higher.

The inhibitor-retarder combination of the present invention is suitable for use over a wide range of temperatures, but temperatures employed with the monomers that are stabilized by the invention typically range from about 60 degrees Celsius to about 180 degrees Celsius.

The inhibitor-retarder combination can be introduced into the monomer to be protected by any conventional method. It can be added as a concentrated solution in suitable solvents just upstream from the point of desired application by any suitable manner. For example, the individual inhibitor and retarder components can be injected separately or in combination to a monomer-containing tank. The individual inhibiting components can also be injected separately along with the incoming feed or through separate entry points, provided there is an efficient distribution of the inhibitor-retarder combination. Since the inhibitors are gradually depleted, it is generally advantageous to maintain the appropriate amount of the inhibitor mixture in the tank in increments over time. Adding inhibitors can be done either on a generally continuous basis or intermittently, in order to maintain the concentration of inhibitor mixture above the minimum required level. In at least one embodiment the method further comprises the step of adding tertiary-butylcatechol. The tertiary-butylcatechol functions as an inhibitor during storage and transport. In at least one embodiment the method further comprises the steps of removing the tertiary-butylcatechol, and producing polystyrene from the monomers.

The foregoing may be better understood by reference to the following examples, which are presented for purposes of illustration and are not intended to limit the scope of the invention.

EXAMPLE 1

In a first example a comparison was made between a sample of a prior art retarder-inhibitor combination comprising HPHA inhibitor and DNBP retarder and a sample of the inventive retarder-inhibitor combination comprising a 7-substituted-quinone methide retarder and an HPHA inhibitor. The retarders were added to each sample at a dosage of 350 ppm relative to monomer weight and the inhibitor was added at a dosage of 150 ppm relative to monomer weight in a continuous stirred tank reactor. The two samples were heated to 120 degrees Celsius and underwent a 1-hour residence. The prior art sample resulted in 539 ppm of unwanted polymer while the inventive retarder-inhibitor combination only had 38.5 ppm of unwanted polymer. This demonstrates that not only is the inventive retarder-inhibitor combination capable of matching the performance of the prior art combination without the toxicity, it in fact has unexpected vastly superior performance.

EXAMPLE 2

In a second example a comparison was made between a sample a prior art retarder-inhibitor combination comprising HPHA inhibitor and DNBP retarder and a sample of the inventive retarder-inhibitor combination comprising a 7-substituted-quinone methide retarder and an HPHA inhibitor. The retarders were added to each sample at a dosage of 350 ppm relative to monomer weight and the inhibitor was added at a dosage of 22.5 ppm relative to monomer weight in a continuous stirred tank reactor.

The two samples were heated to 120 degrees Celsius and underwent a 1-hour residence. The prior art sample resulted in 573 ppm of unwanted polymer while the inventive retarder-inhibitor combination only had 62 ppm of unwanted polymer. This demonstrates that the inventive retarder-inhibitor combination is even capable of drastically preventing the production of unwanted polymer under emergency conditions where additional inhibitor cannot be added.

Changes can be made in the composition, operation, and arrangement of the method of the invention described herein without departing from the concept and scope of the invention as defined in the claims. While this invention may be embodied in many different forms, there are shown and described in detail herein specific preferred embodiments of the invention. The present disclosure is an exemplification of the principles of the invention and is not intended to limit the invention to the particular embodiments illustrated. Furthermore, the invention encompasses any possible combination of some or all of the various embodiments described herein. All patents, patent applications, and references mentioned herein are hereby incorporated by reference in their entirety.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for inhibiting the premature polymerization of monomers by adding to said monomers an effective amount of a composition comprising at least one inhibitor and at least one retarder wherein the inhibitor is an alkylhydroxylamine and the retarder is a 7-substituted-quinone methide selected from the group consisting of: 2,6-di-t-butyl-7-cyano quinone methide, 2,6-di-t-butyl-7-methoxycarbonyl quinone methide, and any combination thereof.

2. The method of claim 1 in which the monomers are vinyl aromatic monomers.

3. The method of claim 1 further comprising an additional inhibitor selected from the group consisting of hydroxypropylhydroxylamine, diethylhydroxylamine, and any combination thereof.

4. The method of claim 1 in which the retarder is non-toxic.

5. The method of claim 1 wherein the inhibitor has a dosage of between 1 to 200 ppm, based on the weight of the monomer.

6. The method of claim 1 wherein the retarder has a dosage of between 1 to 1200 ppm, based on the weight of the monomer.

7. The method of claim 1 in which the inhibitor and retarder are added separately to the monomer.

8. The method of claim 1 in which the amount of inhibitor in the presence of the monomers is maintained at a relatively constant amount by adding the inhibitor in increments over time.

9. The method of claim 1 in which the monomers are in a processing stage.

10. The method of claim 8 in which the inhibitor is added continuously.

11. The method of claim 1 in which the monomers are in solution and the inhibitor is continuously dispersed throughout the solution.

12. The method of claim 1 in which the monomer is at a temperature of between 60 and 180 degrees Celsius.

13. The method of claim 1 in which the monomers are in a manufacturing stage.

14. The method of claim 1 further comprising the step of adding tertiary-butylcatechol, the tertiary-butylcatechol functioning as an inhibitor during storage and transport.

15. The method of claim 14 further comprising the steps of removing the tertiary-butylcatechol, and producing polystyrene from the monomers.

16. A method for inhibiting the premature polymerization of monomers by adding to said monomers an effective amount of a first composition comprising at least one inhibitor and at least one retarder wherein the inhibitor is an alkylhydroxylamine and the retarder is a second composition comprising 2,6-di-t-butyl-7-carboxy quinone methide.

* * * * *